United States Patent [19]
Bitdinger et al.

[11] Patent Number: 5,478,316
[45] Date of Patent: Dec. 26, 1995

[54] AUTOMATIC SELF-INJECTION DEVICE

[75] Inventors: Ralf V. Bitdinger, Herbeys; Jean-Pierre Grimard, Vif, both of France; Bernard Sams, London, England; Donald D. Solomon, Biviers, France

[73] Assignee: Becton, Dickinson and Company, Franklin Lakes, N.J.

[21] Appl. No.: 191,263

[22] Filed: Feb. 2, 1994

[51] Int. Cl.⁶ ................................................. A61M 5/20
[52] U.S. Cl. .................... 604/135; 604/134; 604/136; 604/157; 604/187; 604/192; 604/232
[58] Field of Search ........................... 604/130, 134–138, 604/131, 157, 192, 195, 110, 187, 141, 143, 144, 232

[56] References Cited

U.S. PATENT DOCUMENTS

| | | |
|---|---|---|
| 2,752,918 | 7/1956 | Uytenbogaart . |
| 3,712,301 | 1/1973 | Sarnoff . |
| 3,797,489 | 3/1974 | Sarnoff . |
| 3,882,863 | 5/1975 | Sarnoff et al. . |
| 3,941,130 | 3/1976 | Tibbs . |
| 4,031,893 | 6/1977 | Kaplan et al. . |
| 4,484,910 | 11/1984 | Sarnoff et al. . |
| 4,624,660 | 11/1986 | Mijers et al. . |
| 4,661,098 | 4/1987 | Bekkering et al. . |
| 4,902,279 | 2/1990 | Schmidtz et al. . |
| 5,092,842 | 3/1992 | Bechtold et al. . |
| 5,114,404 | 5/1992 | Paxton et al. . |
| 5,137,516 | 8/1992 | Rand et al. . |
| 5,300,030 | 4/1994 | Crossman et al. . |
| 5,320,609 | 6/1994 | Haber et al. . |
| 5,358,489 | 10/1994 | Wyrick . |

Primary Examiner—C. Fred Rosenbaum
Assistant Examiner—Perry E. Van Over
Attorney, Agent, or Firm—Vincent A. Castiglione

[57] ABSTRACT

A device for automatically injecting a material into the body is disclosed. The device includes a drive assembly and a syringe assembly which is mounted to the drive assembly. The drive assembly includes a drive rod, a driver releasably coupled to the drive rod, and a constant force spring which urges the drive rod towards the syringe assembly. The spring first urges the coupled drive rod and driver along the axis of the device, causing the skin to be penetrated by the needle of the syringe assembly. The drive rod is then decoupled from the driver. The spring continues to urge the drive rod in the axial direction, whereby the drive rod engages a piston in the syringe assembly and causes the displacement of the material therein.

52 Claims, 12 Drawing Sheets

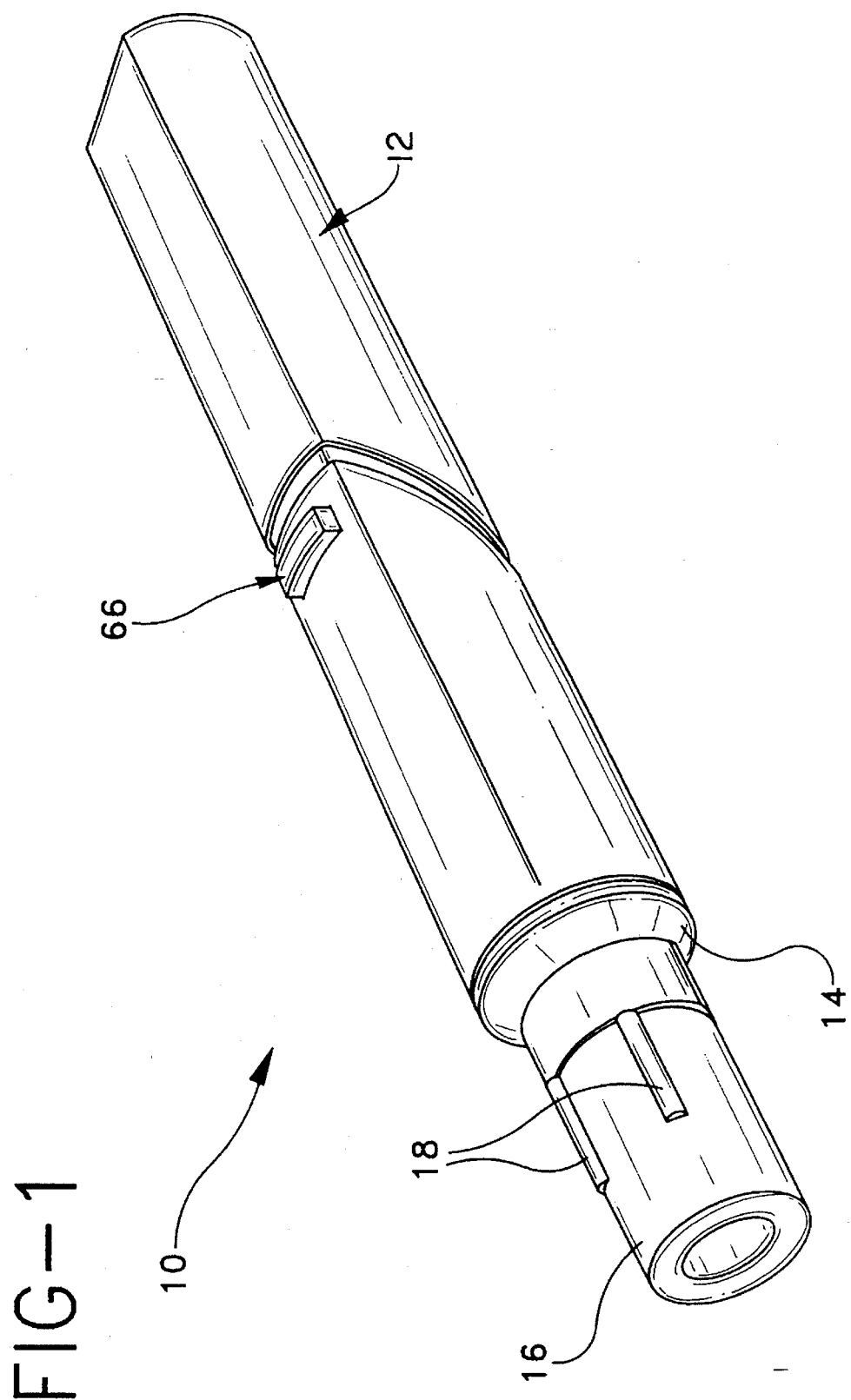

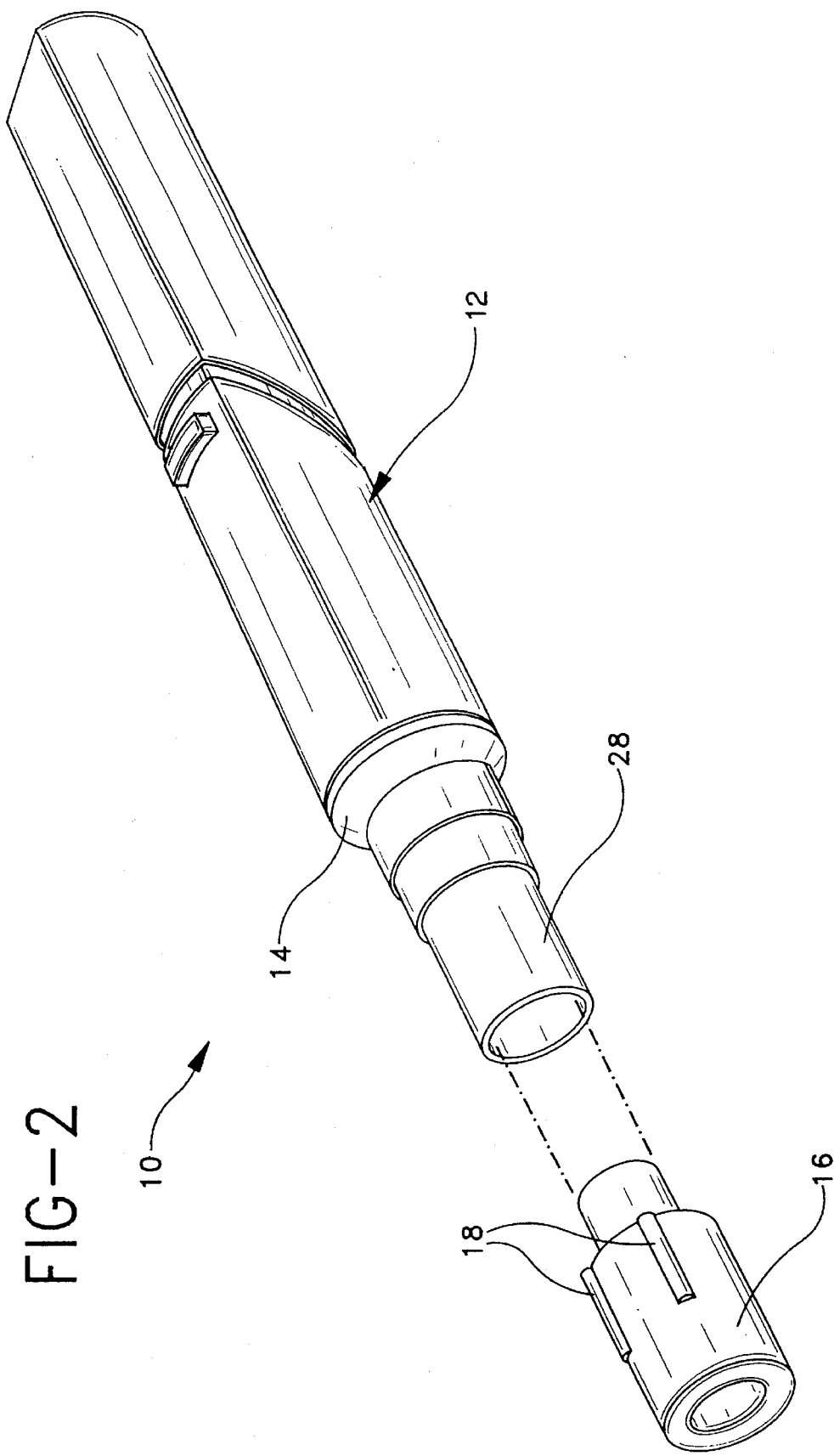

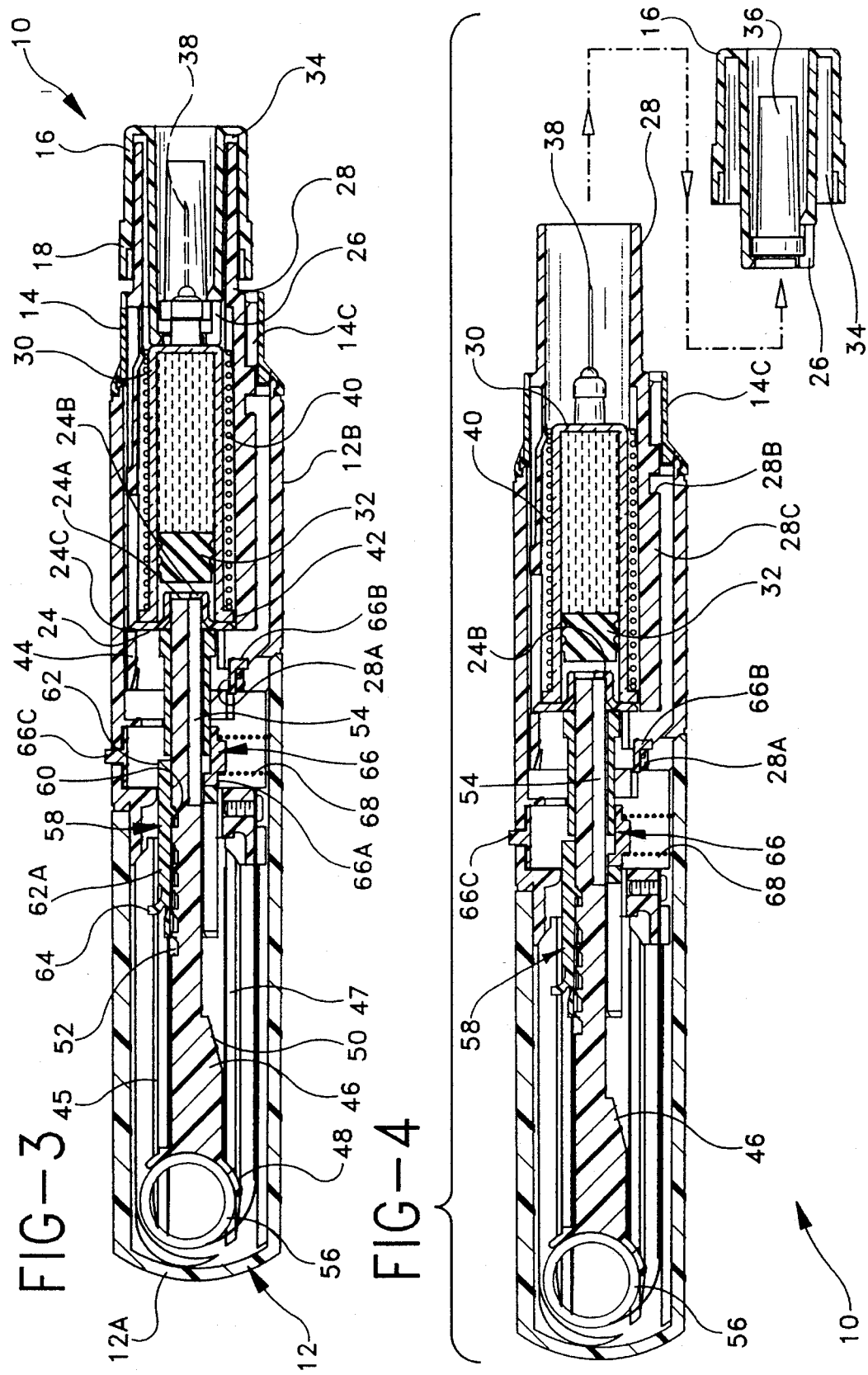

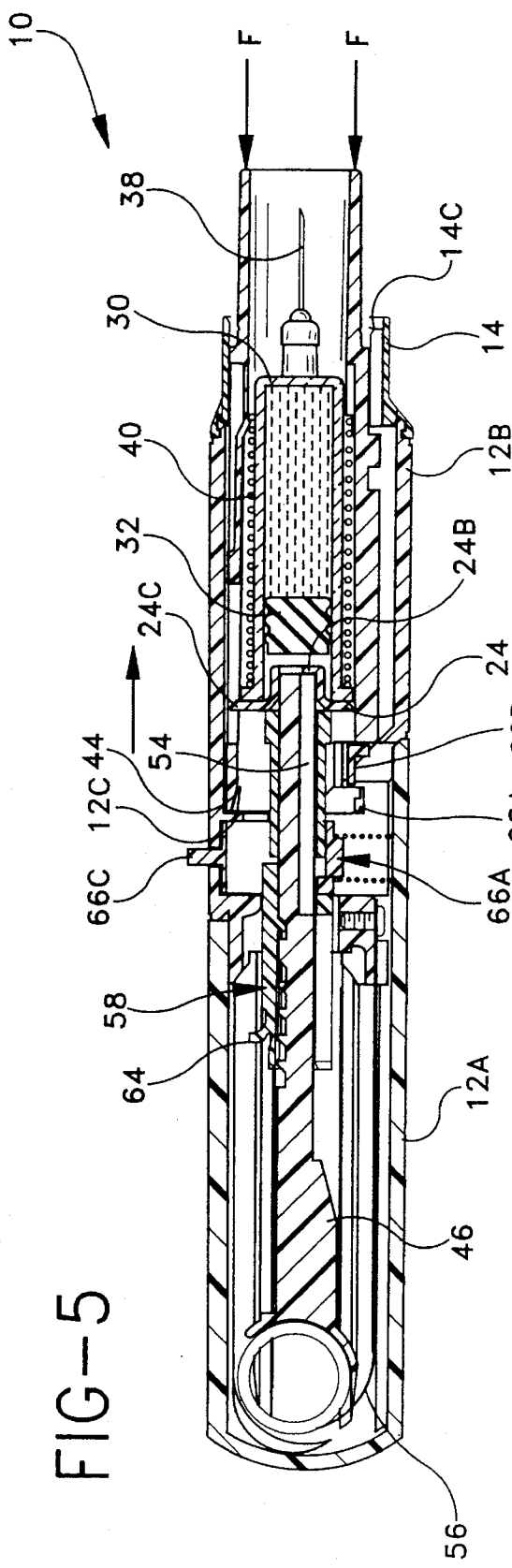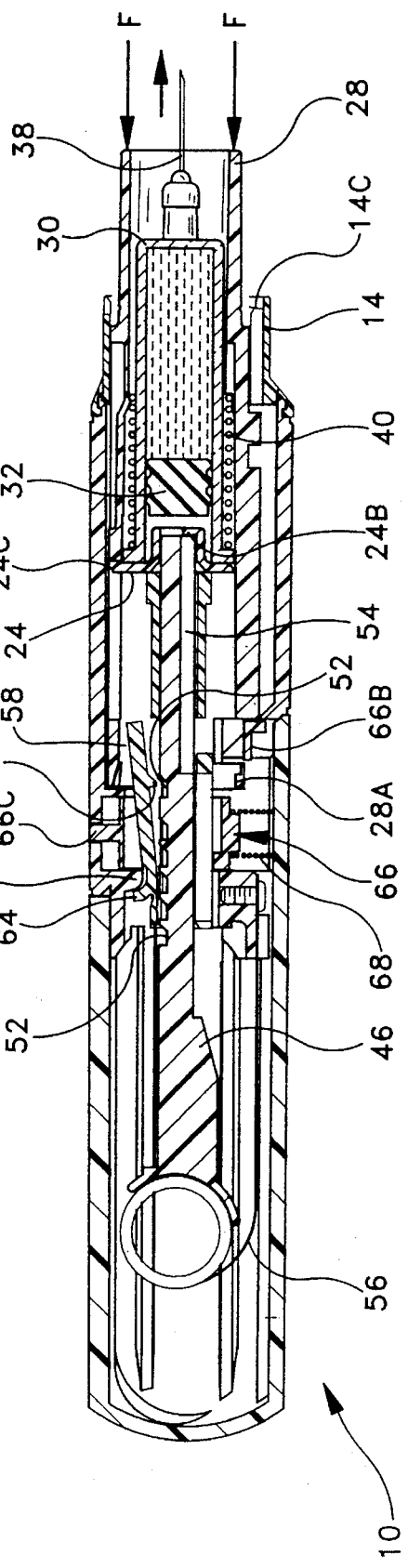
FIG-5
FIG-6

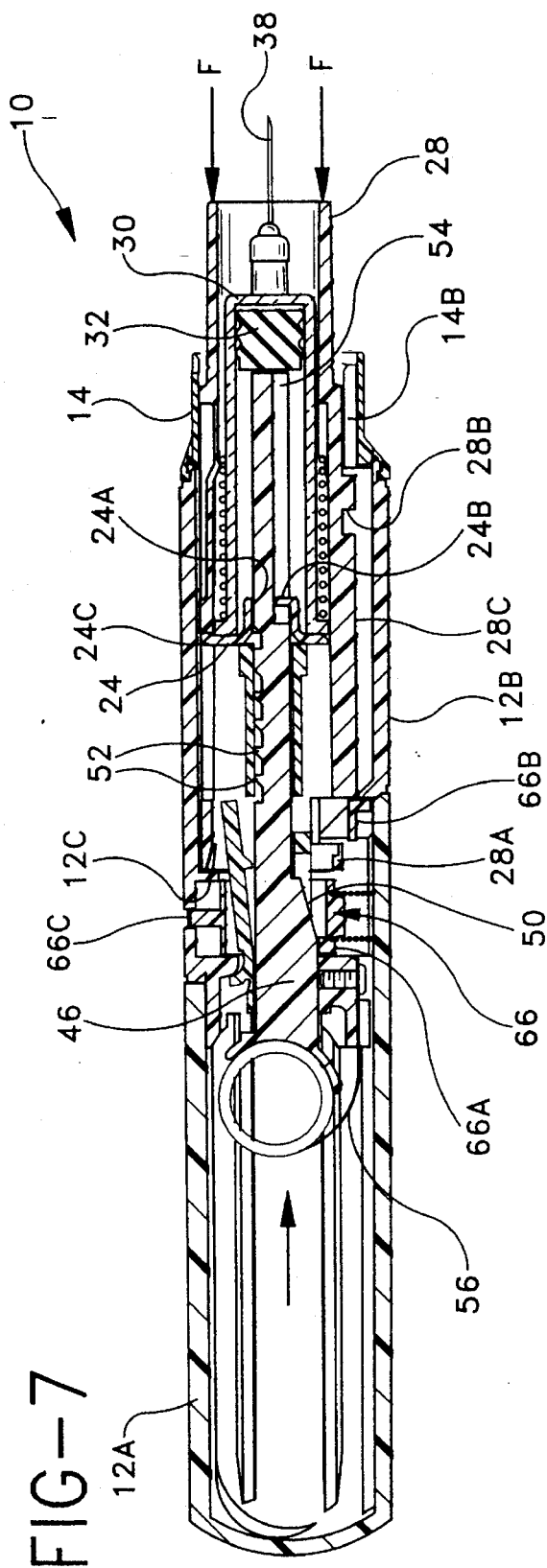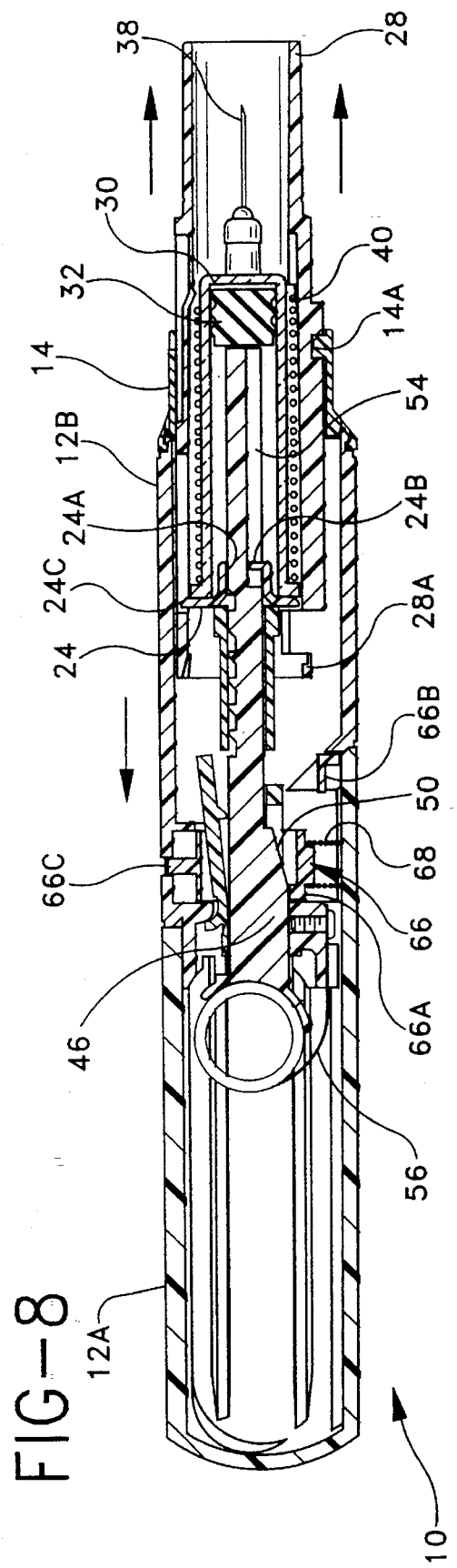

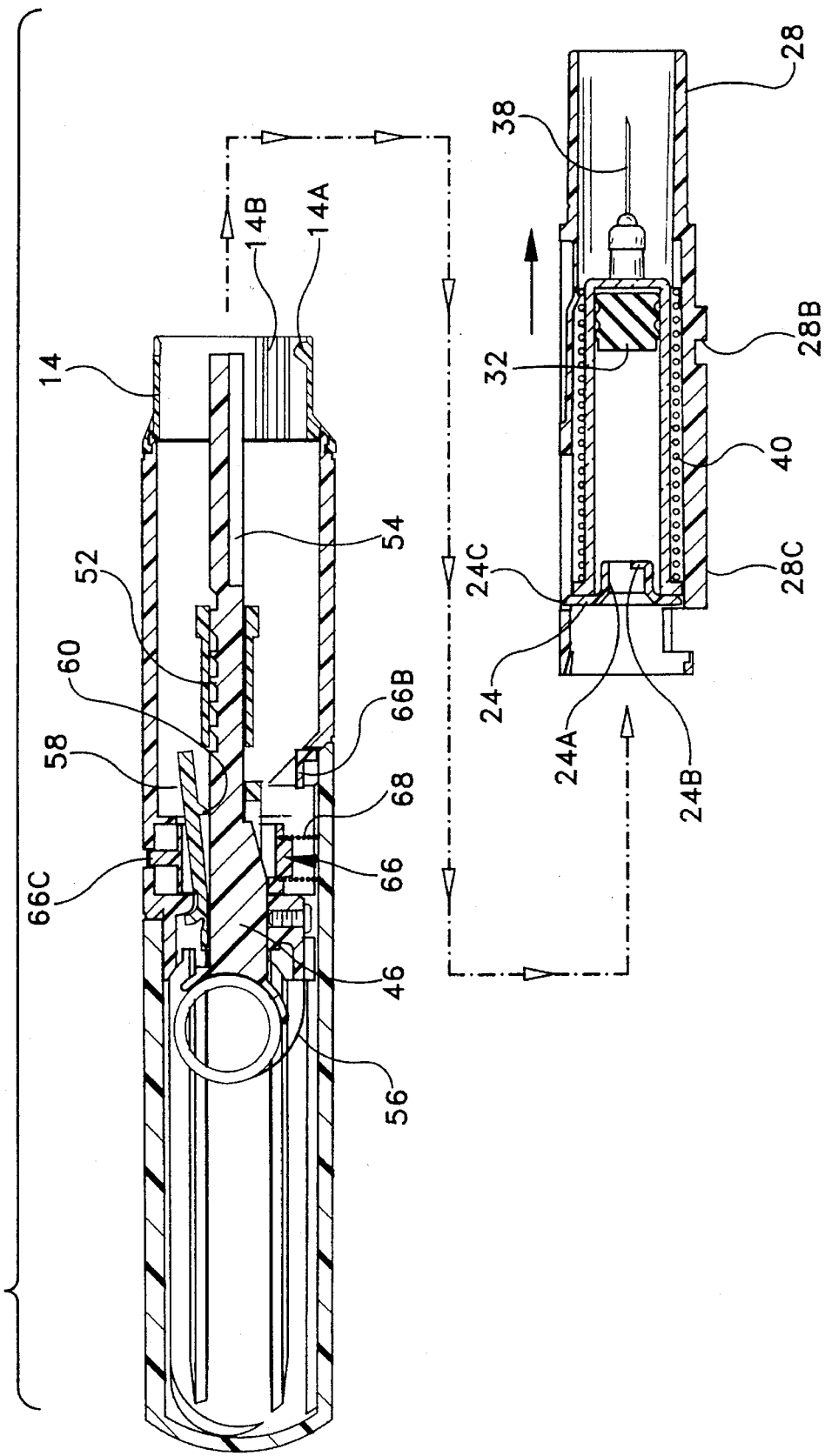

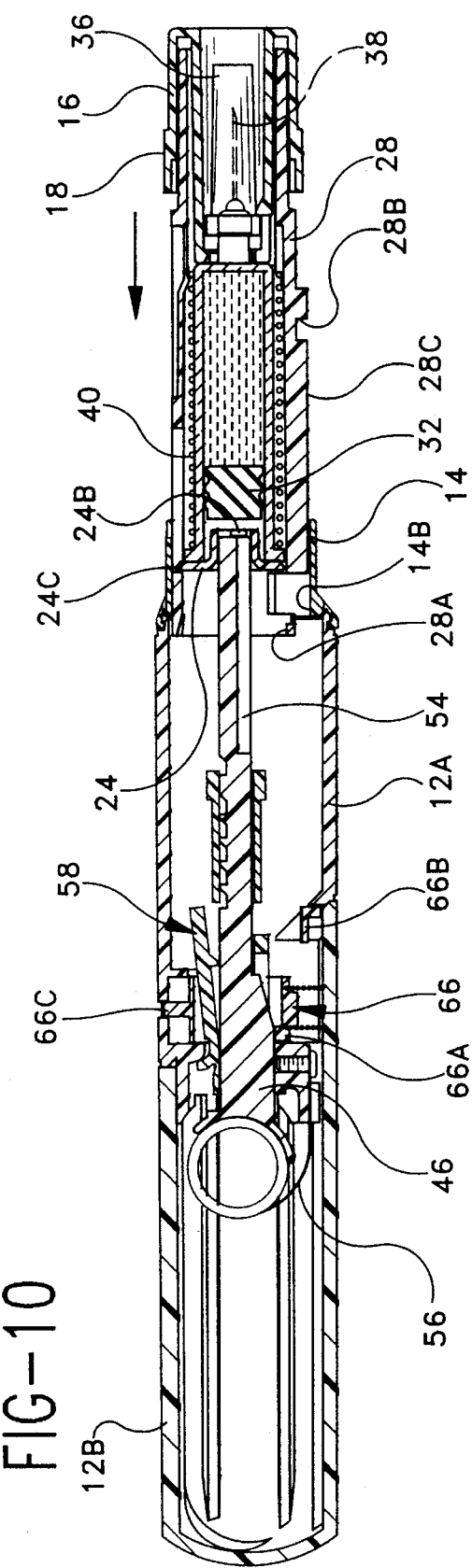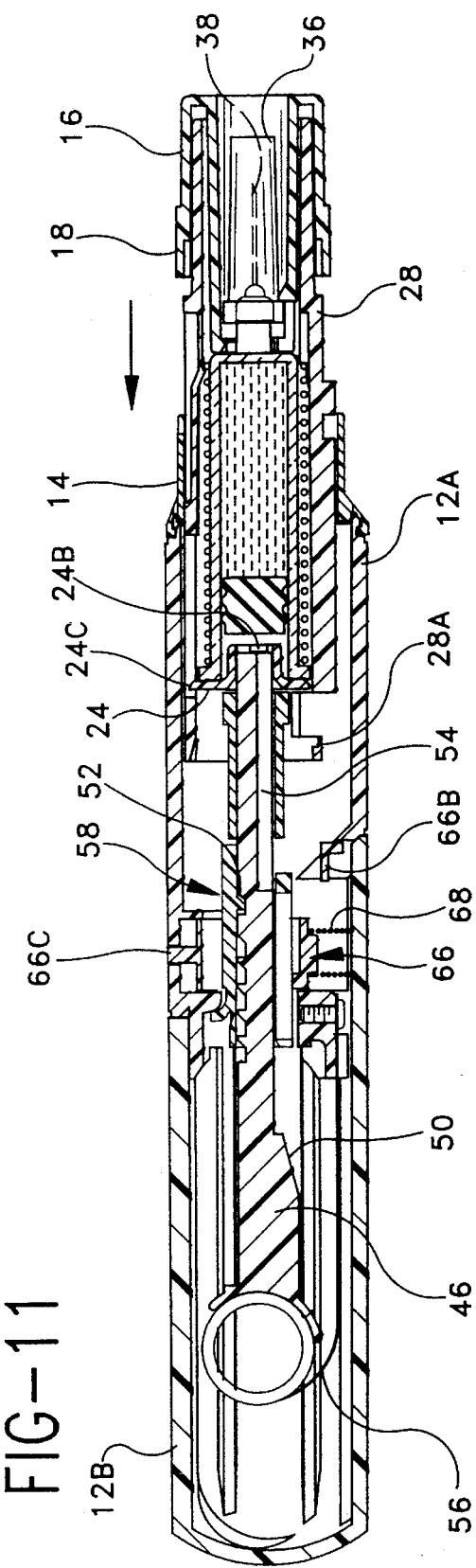

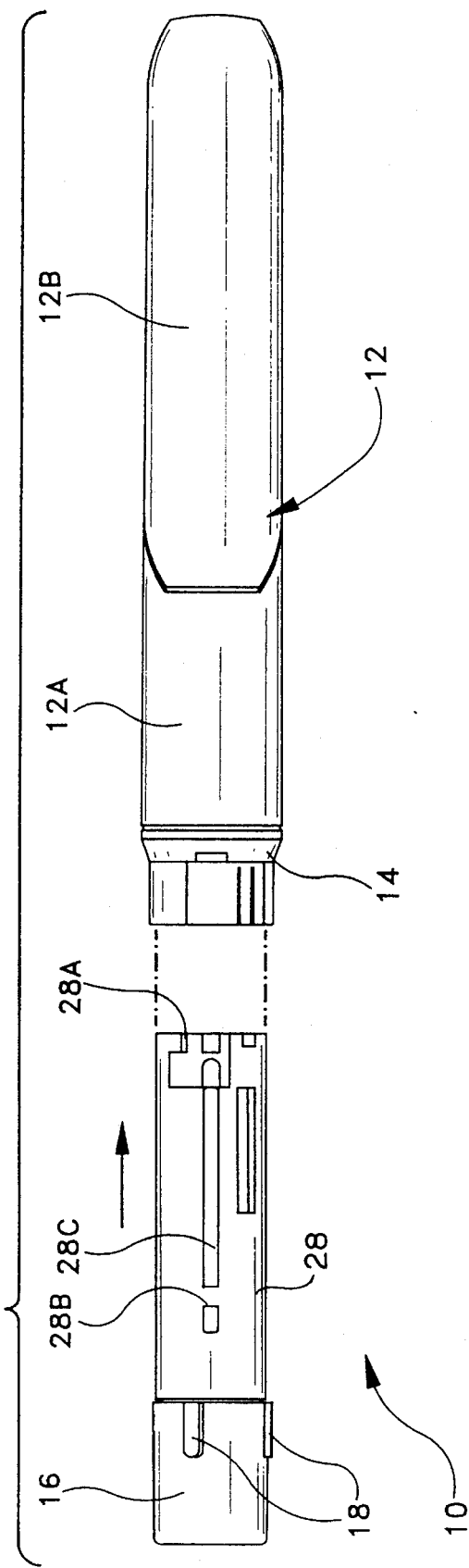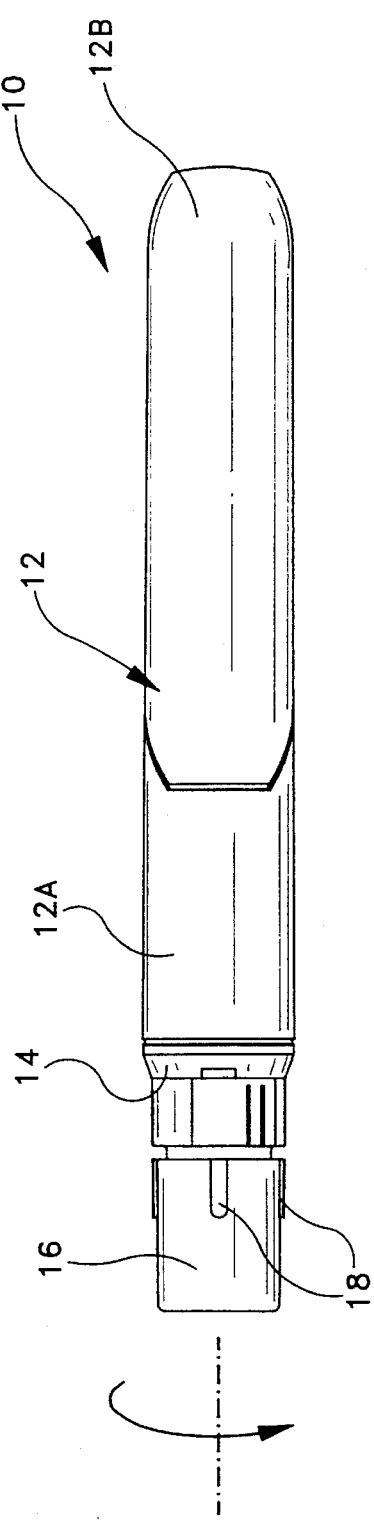

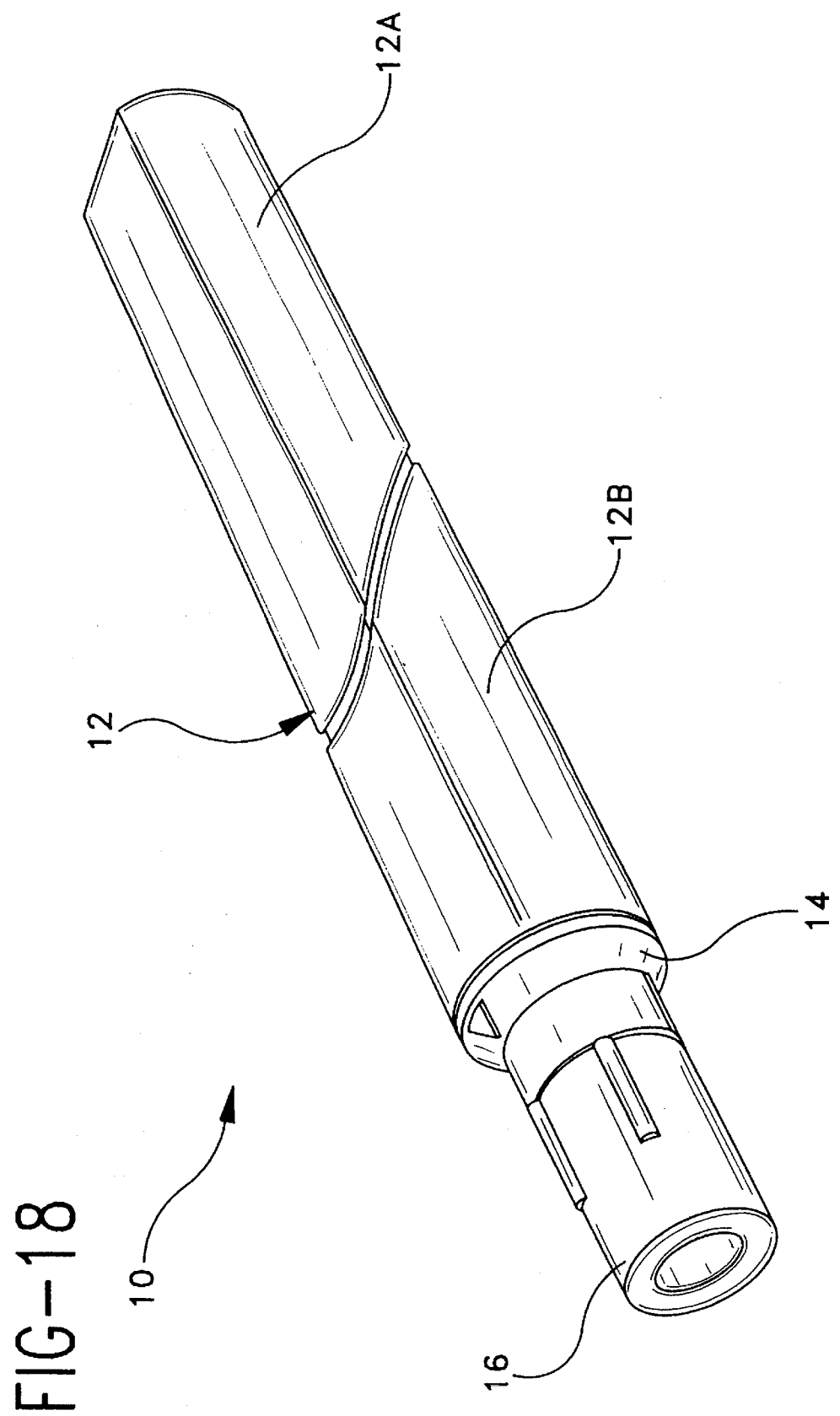

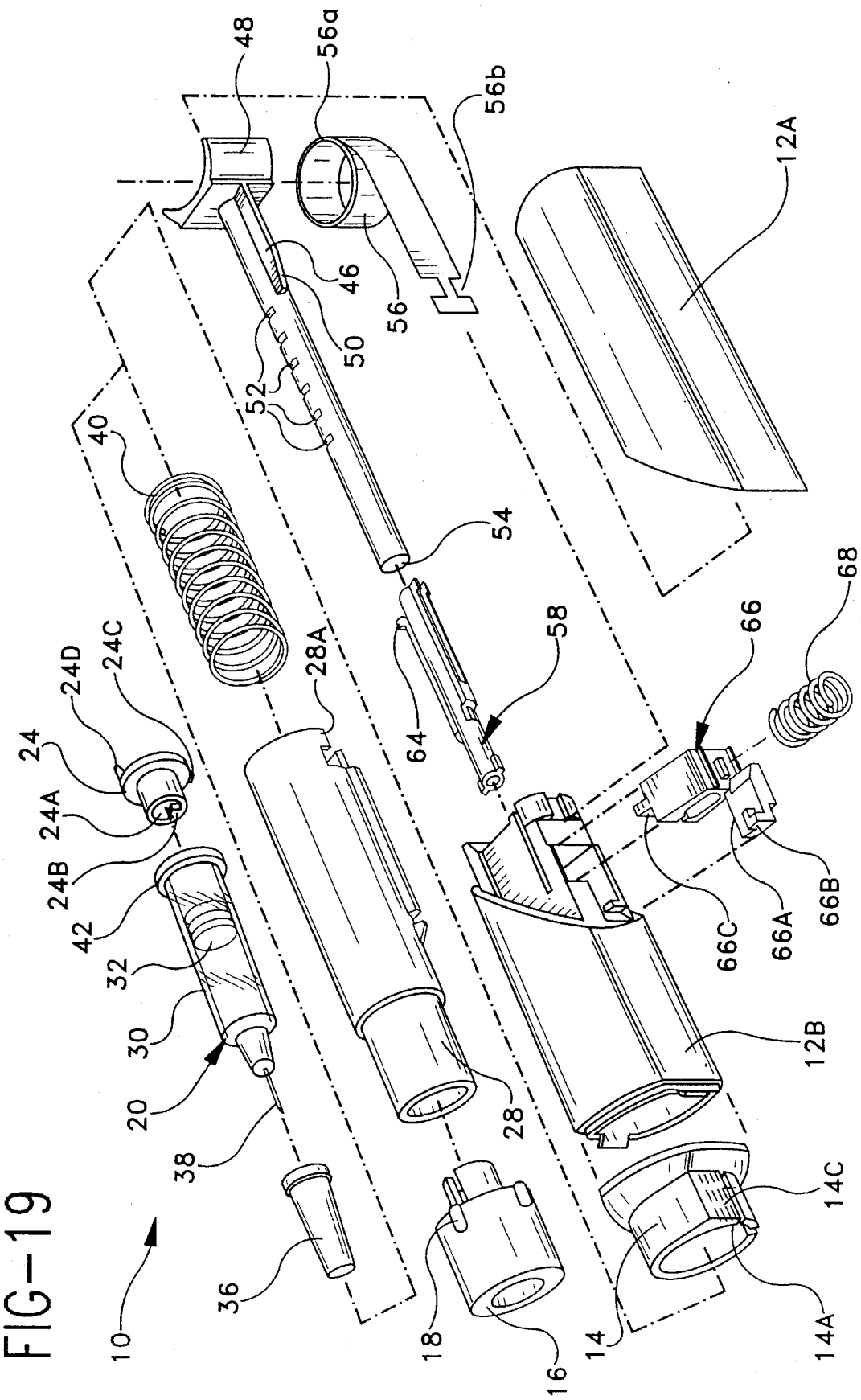

AUTOMATIC SELF-INJECTION DEVICE

BACKGROUND OF THE INVENTION

1. Field of the Invention

The field of the invention relates to injection devices for automatically dispensing premeasured quantities of material, and drive assemblies therefor.

2. Brief Description of the Prior Art

Injection devices such as syringes are widely used in the medical and veterinary fields. They are ordinarily employed by trained personnel who are capable of selecting the appropriate medication and administering the required dosage.

Specialized injection devices have been designed for situations where trained personnel are not available to administer medication. Such devices are usable by persons such as diabetics who self-inject insulin, allergy sufferers who may require an emergency injection of antihistamines or other medication, and other patients where self-injection is either more convenient or necessary.

U.S. Pat. No. 2,752,918 discloses one type of automatically operated injection device. Upon firing an actuating mechanism of this device, a needle is caused to penetrate the skin, medicament is injected through the bore of the needle, and the needle is retracted. The device includes a first coil spring for causing the needle to be projected beyond a nose piece and a second coil spring which is compressed during this procedure. The second spring, upon release of a clutch mechanism, then automatically urges an ampoule and stem rearwardly, causing retraction of the needle.

U.S. Pat. No. 5,137,516 discloses another type of automatically operated injection device. The user first presses the device against the skin in order to move an internal shaft and sleeve assembly. An actuating button is then depressed, causing a button arm to spread the arms of a retention clip. The separation of these arms releases the head of the pusher rod, which is then moved forwardly under the force of a main coil spring. The pusher rod first moves the entire syringe against the force of a syringe spring. Once the needle has penetrated the skin, the syringe plunger is depressed by the pusher rod, causing the syringe to empty. The main spring of the patented device may be recocked upon reloading of a new syringe assembly. Such reloading is accomplished by a force applied by the syringe piston directly upon the pusher rod of the device.

A number of other approaches have been taken for providing automatic injection of various materials. U.S. Pat. Nos. 3,797,489, 4,484,910, 4,902,279 and 5,114,404 provide further examples of this type of device.

SUMMARY OF THE INVENTION

The invention concerns an injection device which is safe to use, reliable, and which minimizes the trauma associated with the self-administration of medicines and materials.

In accordance with a first embodiment of the invention, an injection device is provided which includes a housing, a syringe assembly slidably mounted to the housing, and a constant force spring for moving the syringe assembly with respect to the housing and towards the skin of a patient. By providing a substantially constant force upon the syringe assembly as it moves with respect to the housing, the relatively high impact of coil spring driven devices is avoided. The device is also more easily recocked than devices employing coil springs as the constant force spring does not exert an increasing resistance during the reloading procedure. The constant force spring is preferably employed for driving the piston within the syringe assembly as well as the syringe assembly itself. This is preferably accomplished through the use of a rod and a driver releasably coupled to the rod. The driver causes the syringe assembly to move within the housing until it is decoupled from the rod. The rod then causes the injection of fluid.

In accordance with another embodiment of the invention, the mounting of the syringe assembly to the drive assembly of the device causes the reloading of the drive assembly. To accomplish this function, one end portion of the syringe assembly is provided with an abutment member which engages the drive rod of the drive assembly as it is mounted to the drive assembly. This causes the drive rod to be urged rearwardly against the force of the drive spring until it is retained in a loaded storage position. The abutment member is preferably positioned such that it may be rotated out of engagement with the drive rod, thereby allowing the drive rod to move through the end portion of the syringe assembly to drive the piston in the cartridge or barrel portion thereof. The drive rod preferably includes an elongated groove for receiving the abutment member as it slides through the end portion of the syringe assembly.

A drive assembly for driving a syringe assembly in the manner described above is also provided. The drive assembly includes a drive rod and a driver for urging a syringe piston and syringe assembly, respectively.

Other aspects of the invention which provide important functional advantages include a pushbutton which is drawn within the device at the end of the injection procedure, thereby providing end-of-dose indication. The ability of the pushbutton to release the drive assembly of the device is preferably limited by a sleeve which ordinarily covers the needle assembly. Displacement of the sleeve is necessary before the pushbutton can be moved sufficiently to commence the injection procedure. The sleeve is preferably coupled to the device such that it covers the needle assembly upon disengagement from the skin.

BRIEF DESCRIPTION OF THE DRAWINGS

FIG. 1 is a top perspective view of an injection device according to the invention;

FIG. 2 is a similar view thereof after removal of a cap therefrom;

FIG. 3 is a sectional view thereof showing the device in a storage position;

FIG. 4 is a similar view showing the removal of the cap of the device;

FIG. 5 is a similar view showing the exertion of a force F against the sleeve of the device;

FIG. 6 is a similar view showing the compression of the actuating button, thereby causing the drive spring to drive the syringe assembly;

FIG. 7 is a similar view showing the device upon completion of the injection process;

FIG. 8 is a similar view showing the device upon removal from the skin of a patient;

FIG. 9 is a similar view showing removal of the spent syringe assembly from the drive assembly of the device;

FIG. 10 is a similar view showing the initial step in mounting a new syringe assembly to the drive assembly;

FIG. 11 is a similar view showing the new syringe assembly partially within the housing of the drive assembly;

FIG. 12 is a side elevation view showing the initial step in mounting a new syringe to the drive assembly;

FIG. 13 is a side elevation view showing the final step in mounting a new syringe assembly to the drive assembly;

FIG. 18 is a bottom perspective view of the device, and

FIG. 19 is an exploded, perspective view of the device.

DETAILED DESCRIPTION OF TIME INVENTION

Figure 15:
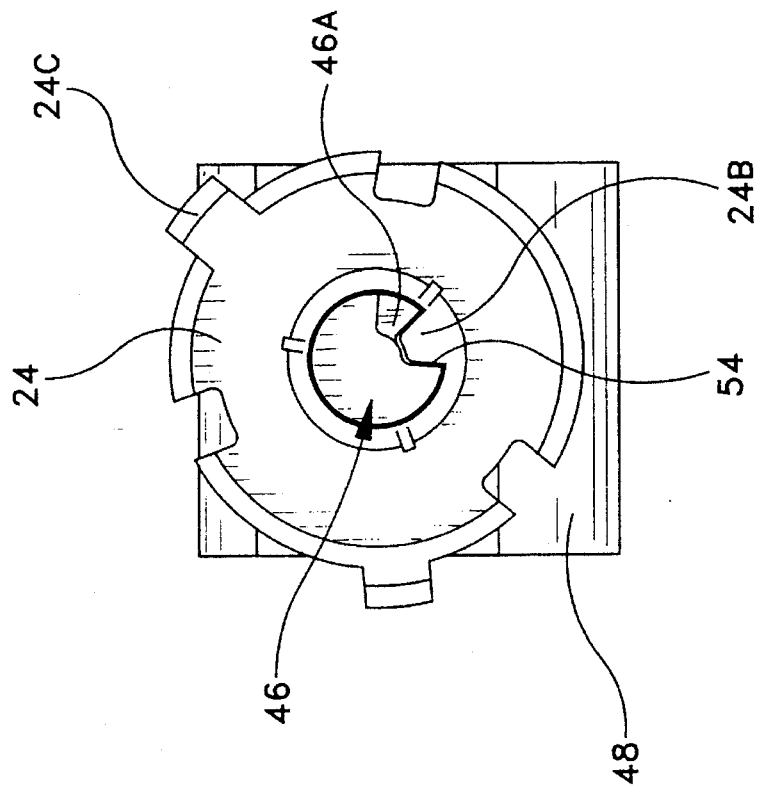
FIG. 15 is a similar view showing the positions of the plug and drive rod after the syringe assembly has been rotated to a selected position.

An injection device 10 is provided which is particularly adapted for the self-administration of medicines and other materials. Referring to FIGS. 1 and 2, the device includes a drive assembly including an elongate housing 12 which may be easily handled by a user. One end of the housing is closed, while the opposite end is mounted to a collar 14. A cap 16 is mounted to one end of a sleeve 28 in adjoining relation to the collar. The cap is not rotatable upon the sleeve, and is employed in conjunction with the collar for mounting a syringe assembly to the drive assembly. A plurality of elongate ribs 18 on the exterior surface of the cap are used during the mounting procedure, which is described in detail below.

FIG. 3 shows the injection device 10 in the storage position. Referring to FIGS. 3 and 19, a syringe assembly 20 is provided in accordance with the preferred embodiment of the invention. A plug 24 mounted to one end of the syringe assembly, and a needle assembly 26 mounted to the opposite end thereof. A sleeve 28 encloses the syringe assembly. The syringe assembly includes a cartridge 30 or barrel and a piston 32 slidably positioned within the cartridge. The cap 16 is removably mounted to one end of the sleeve. An annular slot 34 is defined by a pair of concentric walls of the cap. The end portion of the sleeve 28 is positioned within the annular slot.

A rubber shield 36 is positioned within the cap, and protects the needle 38 of the syringe assembly. The shield is frictionally retained by the cap, and is removable with the cap when the device is to be employed. Rotation of the cap causes rotation of the syringe assembly 20 and sleeve 28 with respect to the drive assembly.

A coil spring 40 is provided for resiliently urging the sleeve 28 with respect to the cartridge 30. The cartridge includes a flange 42 which abuts against one end of the spring. The other end of the spring engages a radially inwardly extending wall of the sleeve. A portion 44 of the sleeve extends behind the plug 24, thereby preventing the sleeve and plug from being disconnected from the syringe assembly. The spring 40 causes the sleeve to extend over the needle in its rest position, as shown in FIGS. 3 and 9.

The drive assembly 45 of the device is designed for repeated use. The drive assembly housing 12 is comprised of two sections 12A, 12B secured to each other by ultrasonic welding or other suitable procedure. An elongate drive rod 46 is positioned within the housing. Guide rails 47 integral with the housing 12 maintain the orientation of the rod. The rod 46 includes an integral saddle 48 at one end thereof. The opposite end of the rod is smaller in dimension such that it fits within the plug 24 and cartridge 30. A ramp 50 is defined on one side of the rod near the saddle end thereof. The opposite side of the rod includes a plurality of notches 52. An elongate groove 54 extends from the end of the rod within the cartridge for a distance corresponding to at least the maximum length of travel of the piston 32 within the cartridge 30.

A constant force spring 56 is provided for urging the rod 46 in the direction of the piston 32. The wound end 56a of the spring 56 is cradled within the saddle 48. The other end 56b of the spring is secured to the housing 12. While a coil spring could be used to propel the rod, such a spring does not exert a substantially constant force upon the rod as it moves axially through the housing. In order to insure that a coil spring exerts sufficient force at the end of the stroke of the rod, it must be compressed more than is actually required at the beginning of the stroke. This results in a relatively high impact upon the syringe assembly by the driving mechanism, and ultimately upon the epidermis of the patient. Such a driving mechanism is also more likely to be very audible to the user, which may tend to upset the user.

The force exerted by the constant force spring 56 is sufficient to overcome the friction between the piston 32 and the cartridge 30 and between the needle 38 and the user's skin. When the rod 46 is pushed back to the start position after firing, the user needs to exert only a constant force upon the rod. If a coil spring was employed in the drive assembly, a steadily increasing force would be required to reload the device.

A driver 58 is releasably coupled to the rod 46. The driver includes a generally cylindrical body through which the rod 46 extends. A radially inwardly extending pawl 60 is positioned within one of the notches 52 and connects the driver to the rod. The pawl 60 extends from a deflectable spring arm 62 of the driver. One end 62A of the arm includes a radially outwardly extending projection 64. One end of the driver abuts against the plug 24.

A pushbutton 66 is provided for engaging both the driver 58 and the sleeve 28. The pushbutton accordingly functions as retaining means for retaining the rod/driver assembly and the constant force spring in the storage position shown in FIG. 3, as well as an actuating member for releasing the retaining means. Referring to FIG. 3, the pushbutton includes a first engagement member 66A which releasably engages the driver. (Alternatively, the rod could be releasably engaged). It further includes a second engagement member 66B which engages a projection 28A of the sleeve. The second engagement member prevents the sleeve from being removed from the drive assembly, and also prevents the pushbutton from being inadvertently actuated.

The pushbutton further includes a projection 66C which extends through an opening in the housing 12. The pushbutton and projection are maintained in the position shown in FIG. 3 by a coil spring 68 which urges the pushbutton towards the opening, as well as by the sleeve projection 28A. When the sleeve projection is displaced rearwardly, as shown in FIG. 5, the coil spring 68 alone maintains the position of the pushbutton.

The first engagement member 66A of the pushbutton may be moved out of engagement with the driver 58 upon manually urging the pushbutton against the force of the compression spring 68. FIG. 6 shows the device shortly after release of the driver/rod assembly. Upon further travel of the driver/rod assembly, as shown in FIG. 7, the ramp 50 defined on one side of the rod 46 engages the first engagement member 66A, thereby drawing the pushbutton further inside the housing 12. This movement causes the release of the sleeve 28, which is urged by the sleeve spring 40 into a position covering the tip of the needle 38 (FIG. 8).

Figure 14:
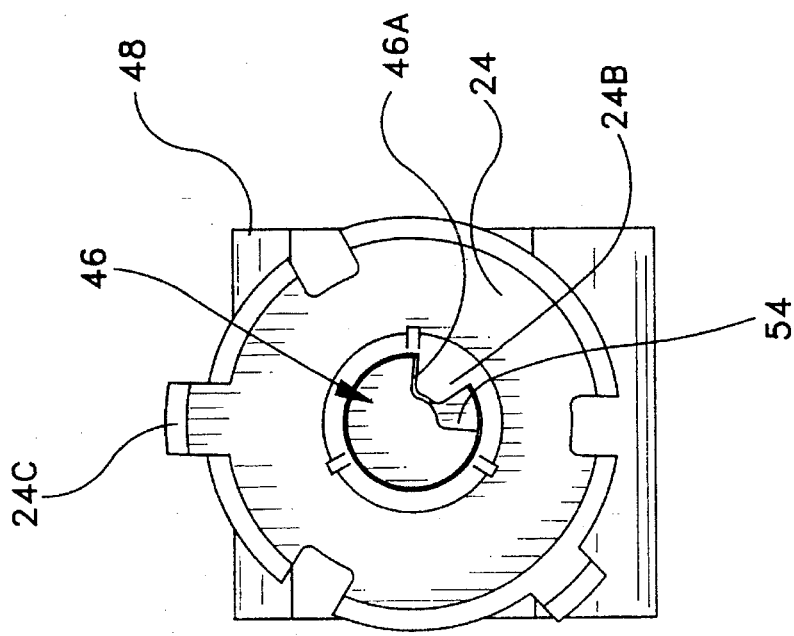
FIG. 14 is an enlarged front end view showing a plug and drive rod of the device in position to load a new syringe assembly.
Figure 17:
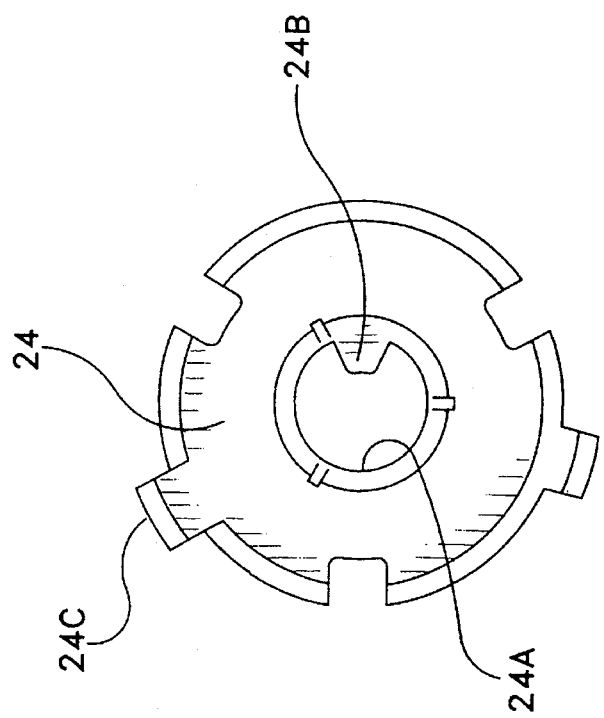
FIG. 17 is a front end view of the plug.
Figure 16:
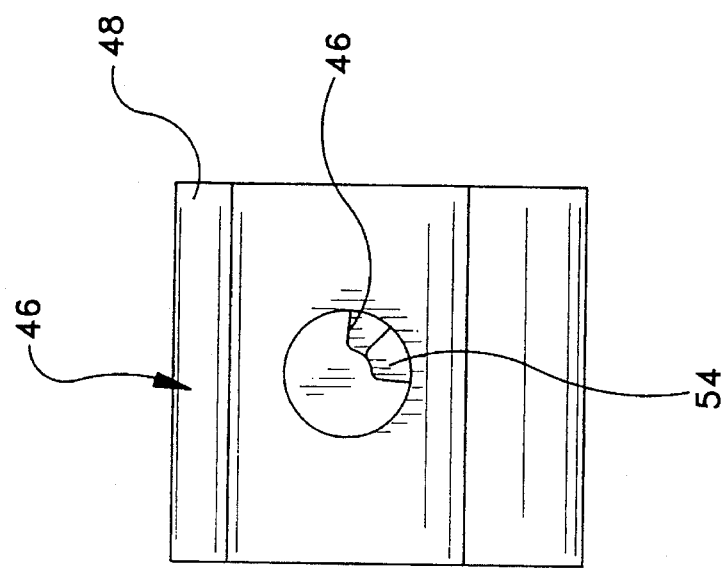
FIG. 16 is a front end view of the drive rod.

As discussed above, the plug 24 is mounted to one end of the syringe assembly 20, and an end of the driver 58 engages the plug. The plug includes an opening 24A through which the rod 46 passes when an injection is made. The plug further includes an abutment in the form of a radially inwardly extending projection 24B, as shown in FIGS. 3–9, 14, 15 and 17. The syringe assembly is rotatable between a first position, as shown in FIGS. 14, where the projection 24B abuts an end surface 46A of the rod, and a second position (FIGS. 3 and 15) where the projection 24B is opposite the groove 54 in the rod. The rod is accordingly able to pass through the plug when the syringe assembly is in the second rotational position. About forty degrees of rotation are required to move the syringe assembly between the first and second positions.

The plug 24 further includes a radially outwardly extending projection 24C which is located within an axial slot 28D in the sleeve. An axial projection 24D extends from the plug, and may be used for alignment purposes when a new syringe assembly is loaded.

The housing 12 includes means for engaging the projection 64 of the driver, thereby causing the arm 62 thereof to pivot about an integral hinge portion as shown in FIG. 6. This, in turn, causes the pawl 60 to be withdrawn from the notch 52. The engaging means include a radially inwardly extending projection 70 having an arcuate surface which engages a corresponding arcuate surface on the projection 64.

The operation of the device will be described with reference to FIGS. 3–11 and 13–15. FIG. 3 shows the device in its storage position. The cartridge 30 contains the material to be injected, and the piston 32 is located towards the rear end of the cartridge. The radially inwardly extending projection 24B of the plug 24 is located opposite the groove 54 in the rod 46. The driver 58 is coupled to the drive rod 46. The pushbutton 66 engages the driver 58, thereby preventing movement of the rod/driver assembly under the force of the constant force spring 56. The pushbutton cannot be depressed to release the rod/driver assembly as the sleeve projection 28A abuts the second engagement member 66B of the pushbutton.

As shown in FIG. 4, the cap 16 is removed by pulling it forwardly along the longitudinal axis of the device. The shield 36 is removed with the cap. The device otherwise remains unchanged from the position shown in FIG. 3.

The end of the sleeve 28 is pressed against the epidermis, thereby causing a force F to be exerted thereon as shown in FIG. 5. The sleeve moves rearwardly against the force of the sleeve spring 40 for several millimeters, at which time the rear portion 44 of the sleeve engages a stop 12C extending from the housing 12. This movement is sufficient to displace the sleeve projection 28A a sufficient distance that it no longer interferes with the downward movement of the pushbutton 66.

The projection 66C of the pushbutton is pressed manually towards the housing as shown in FIG. 6. This causes displacement of the first engagement member 66A such that it no longer engages the driver 58. The driver 58 and rod 46 move as a unit under the constant force of the spring 56, causing the syringe assembly 20 (via the plug 24) to move forwardly, and the needle 38 thereof to penetrate the skin. As the rod remains coupled to the driver, the piston 32 does not move. Once the needle has sufficiently penetrated the skin and underlying tissue, the projection 64 on the driver 58 engages the projection 70 extending inwardly from the housing 12. This causes the pivotable arm 62 of the driver to rotate, and the pawl 60 to move out of the notch 52. The driver 58 and rod are decoupled at this point, which is just prior to the bottoming of the sleeve spring 40.

Referring now to FIG. 7, the rod 46 is urged forwardly as the rear end of the constant force spring 56 rotates within the saddle 48. The rod now moves with respect to the driver 58, urging the piston 32 forwardly as fluid is displaced from the cartridge 30. The rod advances through the plug 24 as the groove 54 is aligned with the plug projection 24B. Movement of the rod continues until the piston 32 engages the end wall of the cartridge 30. The ramp 50 of the rod 46 engages the first engagement member 66A of the pushbutton near the end of its stroke, drawing the pushbutton entirely within the housing. This provides a visual end of dose indication. The sleeve 28 is released once the second engagement member 66B is sufficiently displaced with respect to the sleeve projection 28A.

Upon completion of the injection procedure, the device 10 is withdrawn from the body. The sleeve 28 moves forwardly under the force of the sleeve spring to again cover the needle 38, as shown in FIG. 8, and is releasably locked in position by a pawl 14A. The pushbutton remains within the housing, and accordingly cannot be actuated until a new syringe assembly is installed.

The disposable portion of the device is disconnected from the reusable portion by grasping the sleeve 28 and pulling it in the axial direction. This causes the displacement of the pawl 14A extending radially inwardly from the collar, from a notch 28B within the sleeve. The cap 16 can be replaced before or after removal of the disposable portion of the device.

A new syringe assembly is installed by grasping the cap 16 and aligning a longitudinal rib 28C on the sleeve with a slot 14B in the collar. It can then be pushed into the housing until the cap 16 engages the collar 14. When aligned in this manner, the plug projection 24B is in opposing relation to the end surface 46A of the rod rather than the groove 54 within the rod. Insertion of the disposable portion of the device 10 accordingly causes the rod 46 to be pushed back into the housing 12. The wound end of the constant force spring 56 rotates in the saddle as the spring unravels. The rim of the plug 24 pushes back the driver 58 during this procedure.

The disposable portion can be rotated about an arc of forty degrees once it is pushed as far back as possible. Because the driver is pushed back with the rod, the pushbutton 66 springs back into the position shown in FIG. 3 as it moves partially within the gap of the driver. The driver pawl 60 moves into one of the notches 52 in the rod. The particular notch to be engaged by the pawl is determined by the length of the plug 24. If the piston 32 is located closer to the needle end of the cartridge, the nose portion of the plug will be longer such that is adjoins, but does not contact, the piston.

It will be appreciated that various modifications can be made to the device for various purposes. While not preferred, a pair of springs could be used to drive the syringe assembly and piston, respectively. One or both springs could be constant force springs, preferably both. While it is also highly preferred that the drive assembly be rearmed upon insertion of the syringe assembly, this step could also be accomplished as a separate procedure. The use of a constant force spring facilitates the rearming procedure regardless of which approach is employed. Rearming may also be accomplished without directly engaging the drive rod. It is sufficient that the rod be driven back against the force of the drive spring, whether by direct engagement of the rod or via an intermediate structure.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An automatic injection device comprising:

a housing;

a syringe assembly slidably mounted to said housing, said syringe assembly including a cartridge and a piston slidably mounted within said cartridge;

means for causing said syringe assembly to slide with respect to said housing from a storage position to a deployed position, said means for causing including a constant force spring having one end secured to said housing and a second end variably wound with respect to said syringe assembly to provide a substantially constant force upon said syringe assembly between said storage and deployed positions;

means for causing said piston to slide within said cartridge from a first position to a second position such that the contents of said cartridge are expelled, and means for releasably retaining said constant force spring in a selected position.

2. A device as described in claim 1, wherein said means for causing said piston to slide within said cartridge include said constant force spring.

3. A device as described in claim 2, including a sleeve mounted to said housing, said sleeve including a first end portion adapted to engage the skin of a patient, a spring urging said sleeve in the direction of said first end portion, said sleeve being retractable with respect to said housing against the force of said spring when sufficient pressure is exerted against said first portion.

4. A device as described in claim 3 including a manually operated actuating member for releasing said constant force spring retaining means.

5. A device as described in claim 4 including means for selectively preventing said actuating member from releasing said constant force spring retaining means, said means for selectively preventing being coupled to said sleeve.

6. A device as described in claim 2 including an elongate rod, a driver releasably coupled to said elongate rod, means for decoupling said elongate rod from said driver, said second end of the constant force spring variably wound with a portion of said elongate rod, said driver being engageable with said syringe assembly for moving said syringe assembly with respect to said housing, said elongate rod being engageable with said piston for moving said piston with respect to said cartridge, said constant force spring urging said driver and elongate rod towards said syringe assembly and piston, respectively.

7. A device as described in claim 6, wherein said elongate rod includes at least one notch, said driver includes a first projection extending radially inwardly within said notch and a second projection extending radically outwardly, said means for decoupling including means for engaging said second projection, thereby causing said first projection to be withdrawn from said notch.

8. A device as described in claim 6, including a manually operated actuating member extending at least partially from said housing, and said elongate rod includes means for drawing said actuating member within said housing.

9. A device as described in claim 1 including a sleeve releasably mounted to said housing and enclosing at least part of said syringe assembly.

10. A device as described in claim 9 including an elongate rod slidably mounted within said housing and engageable with said piston, said second end of the constant force spring variably wound with a portion of said elongate rod for urging said elongate rod towards said piston; and a plug mounted to said cartridge, said plug including an abutment engageable with said rod when said plug is in a first rotational position, said rod being movable through said plug when said plug is in a second rotational position.

11. A device as described in claim 6, including a plug mounted to one end of said syringe assembly, said plug including an abutment adjoining an end surface of said elongate rod when said cartridge is in a first rotational position, said syringe assembly being rotatable to a second rotational position wherein said abutment does not adjoin said end surface of said elongate rod, thereby allowing at least a portion of said elongate rod to pass through said plug.

12. A device as described in claim 11, wherein said driver engages said plug.

13. An automatic injection device comprising:

a housing having a longitudinal axis;

a cartridge mounted within said housing;

a piston slidably mounted within said cartridge;

a needle assembly mounted to said cartridge;

a rod;

a driver releasably coupled to said rod;

a constant force spring having one end secured to said housing and a second end variably wound with respect to a portion of said rod for urging said rod along the longitudinal axis of said housing such that said driver urges said cartridge and said rod urges said piston along the longitudinal axis, and means for automatically decoupling said driver and said rod as said rod moves along the longitudinal axis such that said rod moves said piston with respect to said cartridge upon said driver being decoupled from said rod.

14. A device as described in claim 13 including a sleeve, said cartridge being mounted within said sleeve, said sleeve including a first open end adjoining said needle assembly and a second end, said second end including a radially inwardly extending abutment, said sleeve being rotatable between a first rotational position wherein said abutment engages an end surface of said rod, thereby allowing said rod to be moved axially against the force of said constant force spring as said sleeve is moved within said housing, and a second rotational position wherein said abutment does not engage said end surface of said rod, thereby allowing said rod to move at least partially through said second end of said sleeve and drive said piston within said cartridge.

15. A device as described in claim 14, wherein said rod includes an elongate groove, said abutment being positioned within said groove when said rod moves through said second end of said sleeve.

16. A device as described in claim 14 including a coil spring, said cartridge being positioned within said coil spring and engaging said coil spring, said coil spring also engaging said sleeve and urging said sleeve along said longitudinal axis.

17. A device as described in claim 13, wherein said rod includes a notch and said driver includes a pawl positioned within said notch, said housing including means for engaging said driver such that said pawl is withdrawn from said notch.

18. A device as described in claim 13 including releasable retaining means for retaining said rod in a storage position against the force of said constant force spring.

19. An assembly for providing automatic injections, comprising:
- a syringe assembly including a cartridge, a piston slidably mounted within said cartridge, a first end portion including a needle assembly mounted to said cartridge, and a second end portion including an abutment member;
- a drive assembly including a housing having an open end, a rod slidably mounted within said housing, a spring having one end secured to the housing and a second end engaged with said rod for resiliently urging said rod towards the open end of said housing, and retaining means for releasably retaining said rod in a storage position against the force of said spring, and
- means for releasably connecting said syringe assembly and said drive assembly,
- said abutment member being engageable with said rod when said syringe assembly is moved into the open end of said housing of said drive assembly, thereby urging said rod away from said open end against the force of said spring.

20. An assembly as described in claim 19, wherein said abutment member is disengageable with said end of said rod upon rotation of said syringe assembly to a selected position, said rod being movable at least partially through said second end portion of said syringe assembly when said syringe assembly is in said selected position.

21. An assembly as described in claim 20, wherein said syringe assembly includes a sleeve, said cartridge being mounted within said sleeve, said second end portion of said syringe assembly including a plug mounted to said cartridge, said plug including a body portion having a passage extending therethrough, said abutment member extending from said body portion into said passage.

22. An assembly as described in claim 21, wherein said retaining means include a pushbutton mounted to said housing, and said means for releasably connecting said syringe assembly and said drive assembly include abutting surfaces of said pushbutton and said sleeve.

23. An assembly as described in claim 20 including a driver releasably coupled to said rod, said driver member being positioned for engaging said second end portion of said syringe assembly and said rod being positioned for engaging said piston when said syringe assembly is connected to said drive assembly.

24. An assembly as described in claim 20, wherein said spring is a constant force spring having said first end connected to said housing and said second end variably wound with said rod.

25. An assembly as described in claim 20, wherein said rod includes a longitudinal groove aligned with said abutment member when said syringe assembly is in said selected position.

26. A drive assembly for an automatic injection device comprising:
- a housing having a longitudinal axis, a first end, and a second end;
- a drive rod positioned within said housing, said drive rod including a first engagement member;
- a driver including a body having an opening, and a second engagement member, said drive rod extending through said opening such that said second engagement member is engageable with said first engagement member;
- spring means having one end secured to said housing and a second end secured with said drive rod for resiliently urging said drive rod towards said first end of said housing, and
- means for automatically disengaging said second engagement member from said first engagement member as said drive rod moves axially within said housing such that said drive rod moves independently of said driver.

27. An assembly as described in claim 26, wherein said first engagement member is a notch and said second engagement member is a pawl, said body of said driver including a spring arm, said pawl extending from said spring arm.

28. An assembly as described in claim 27, wherein said means for automatically disengaging include a first projection extending from said spring arm and a second projection extending from said housing, said first projection engaging said second projection when said drive rod is in a selected axial position within said housing.

29. An assembly as described in claim 26, wherein said rod extends beyond said driver near said first end of said housing.

30. An assembly as described in claim 26, wherein said spring means for resiliently urging is a constant force spring.

31. An assembly as described in claim 30, wherein said rod includes a saddle at one end thereof, wherein the second end of said constant force spring comprises a wound end positioned within said saddle, said first end secured to said housing.

32. An assembly as described in claim 26 including a pushbutton mounted to said housing, said pushbutton including a projection, said housing including an opening in registration with said projection, said pushbutton further including means for releasably engaging said driver.

33. An assembly as described in claim 32, wherein said drive rod includes a ramp member for engaging said pushbutton and moving said projection within said housing.

34. An assembly as described in claim 26, wherein said first end of said housing includes means for releasably engaging a syringe assembly.

35. An assembly as described in claim 34, wherein said pushbutton includes means for releasably engaging a syringe assembly.

36. An automatic injection device comprising:
- a drive assembly including a housing and a drive rod slidably mounted within said housing;
- a syringe assembly including a cartridge, a piston slidably mounted within said cartridge, and a needle assembly mounted to said cartridge;
- constant force spring means having one end secured to said housing and a second end variably wound with said drive rod for resiliently urging said drive rod towards said syringe assembly;
- means fix releasably retaining said drive rod in a storage position, said means for releasably retaining including a pushbutton slidably mounted to said housing, and
- means for drawing said pushbutton within said housing as said drive rod moves from said storage position to a deployed position.

37. A device as described in claim 36, wherein said means for drawing include a ramp on said drive rod, said ramp being engageable with said pushbutton.

38. A device as described in claim 36 including a driver releasably coupled to said drive rod, said pushbutton engaging said driver when said drive rod is in said storage position.

39. A device as described in claim 36 including a sleeve releasably coupled to said housing, said syringe assembly being mounted within said sleeve, said pushbutton including means for releasably engaging said sleeve, said means for releasably engaging said sleeve being disengaged from said sleeve when said pushbutton is drawn within said housing by said means for drawing.

40. An automatic injection device comprising:

a syringe assembly including a cartridge, a piston slidably mounted within said cartridge, and a needle assembly mounted to said cartridge;

a sleeve, said syringe assembly being positioned at least partially within said sleeve;

a drive assembly coupled to said syringe assembly and including a housing, a first drive member within said housing for driving said syringe assembly, a second drive member within said housing for driving said piston with respect to said cartridge, and constant force spring means having one end secured to said housing and a second end variably wound with said second drive member for resiliently urging said first and second drive members towards said syringe assembly;

a pushbutton movably mounted to said housing, said pushbutton including a projection extending outside said housing, a first engagement member releasably retaining said first and second drive members in a storage position, and a second engagement member, means for slidably mounting said sleeve with respect to said syringe assembly such said sleeve is slidable between first and second axial positions, said second engagement member of said pushbutton being in opposing relation to a portion of said sleeve when said sleeve is in said first axial position such that said portion of said sleeve limits the movability of said pushbutton with respect to said housing, said portion of said sleeve being displaced from said second engagement member when said sleeve is in said second axial position such that said pushbutton can be moved a sufficient distance with respect to said housing to release said first and second drive members from said first engagement member.

41. A device as described in claim 40, wherein said first drive member is a driver and said second drive member is an elongate drive rod releasably coupled to said driver.

42. A device as described in claim 41, wherein said first engagement member engages said driver.

43. A device as described in claim 42 including a spring mounted to said syringe assembly and resiliently urging said sleeve to a position wherein said sleeve covers said needle assembly.

44. A device as described in claim 43, wherein said syringe assembly is movable within said sleeve between a first position wherein said spring is relatively expanded and a second position wherein said spring is relatively compressed.

45. A device as described in claim 41, wherein said housing includes means for decoupling said driver and said drive rod.

46. An automatic injection device comprising:

a syringe assembly including a cartridge, a piston slidably mounted within said cartridge, and a needle assembly mounted to said cartridge;

a drive assembly coupled to said syringe assembly, said drive assembly including a housing, a drive apparatus within said housing, and first means comprising a constant force spring having one end secured to said housing and a second end variably wound with said drive apparatus for resiliently urging said drive apparatus towards said syringe assembly such that said piston is displaced with respect to said cartridge and said syringe assembly is displaced with respect to said housing from a storage to a deployed position;

an elongate sleeve mounted to said cartridge, and second means for resiliently urging said sleeve over said needle assembly, said elongate sleeve being movable by said second means for resiliently urging to a position covering said needle assembly when said syringe assembly is in said deployed position.

47. A device as described in claim 46, wherein said drive apparatus includes a drive rod for driving said piston and a driver for driving said syringe assembly, said driver being releasably coupled to said drive rod.

48. A device as described in claim 47 including means for automatically decoupling said driver and said drive rod.

49. A device as described in claim 46, wherein said second means for resiliently urging is a coil spring having a first end engaging said cartridge and a second end engaging said sleeve.

50. A device as described in claim 49 including a plug mounted to one end of said cartridge, said sleeve including a portion adjoining said plug for retaining said sleeve upon said syringe assembly against the force of said coil spring.

51. A device as described in claim 50, wherein said drive apparatus includes a drive rod having an elongate slot, and said plug includes a radially inwardly extending projection aligned with said elongate slot.

52. A device as described in claim 51, wherein said sleeve includes an elongate slot and said plug includes a radially outwardly extending projection located within said elongate slot of said sleeve.

* * * * *